United States Patent [19]

Mückenmuller et al.

[11] 4,107,027
[45] Aug. 15, 1978

[54] DEVICE FOR CONTINUOUS ELECTROPHORESIS IN A CARRIER FREE BUFFER CURRENT

[75] Inventors: Helmut Mückenmuller, Dossenheim; Hubert Muth, Mauer, both of Fed. Rep. of Germany

[73] Assignee: C. Desaga GmbH, Nachf. Erich Fecht, Heidelberg, Fed. Rep. of Germany

[21] Appl. No.: 777,669

[22] Filed: Mar. 15, 1977

[30] Foreign Application Priority Data

Mar. 20, 1976 [DE] Fed. Rep. of Germany ....... 2612005

[51] Int. Cl.² .................. G01N 27/26; G01N 27/28
[52] U.S. Cl. .................. 204/301; 204/180 R; 204/299 R
[58] Field of Search ............ 204/180 S, 180 G, 299, 204/301, 180 R; 23/230 B

[56] References Cited

U.S. PATENT DOCUMENTS

| | | | |
|---|---|---|---|
| 3,326,790 | 6/1967 | Bergrahm | 204/299 X |
| 3,378,481 | 4/1968 | Saravis et al. | 204/299 |
| 3,766,047 | 10/1973 | Elevitch | 204/299 |
| 3,773,646 | 11/1973 | Mandle et al. | 204/299 |
| 3,856,656 | 12/1974 | Brink | 204/299 |
| 3,875,045 | 4/1975 | Bergrahm et al. | 204/299 |
| 3,888,759 | 6/1975 | Elson et al. | 204/299 |

*Primary Examiner*—Arthur C. Prescott
*Attorney, Agent, or Firm*—Friedman, Goodman & Teitelbaum

[57] ABSTRACT

Device for the continuous electrophoresis in a carrier free buffer current including a separating chamber, in which a separating space is located between two plane parallel glass plates held in a two-part frame and is separated from electrode chambers by permeable membranes. A dividing joint is provided between two frame-parts at least partially at an angle to a dividing plane of the frame located between and parallel to the glass plates. The membranes, when the frame-parts are pressed together along the dividing joint, are pressed against the surfaces of the frame-parts which form a part of the dividing joint, with a force component lying in the direction of the dividing plane, thus forming a seal. The separating chamber permits easy assembly and disassembly thereof.

13 Claims, 2 Drawing Figures

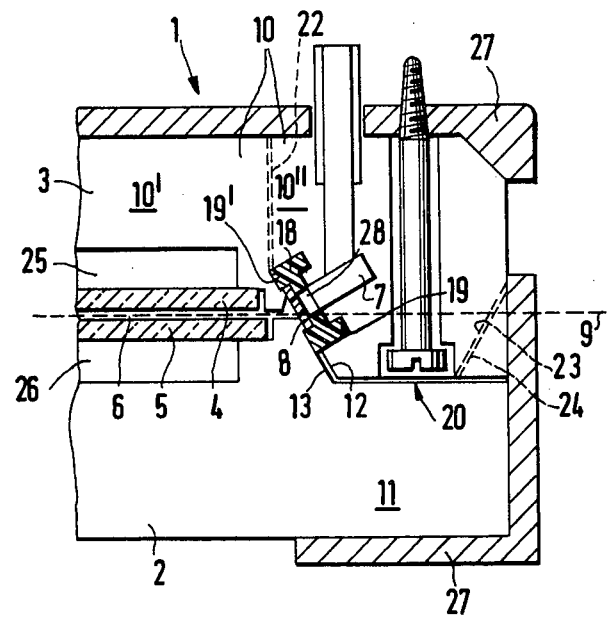
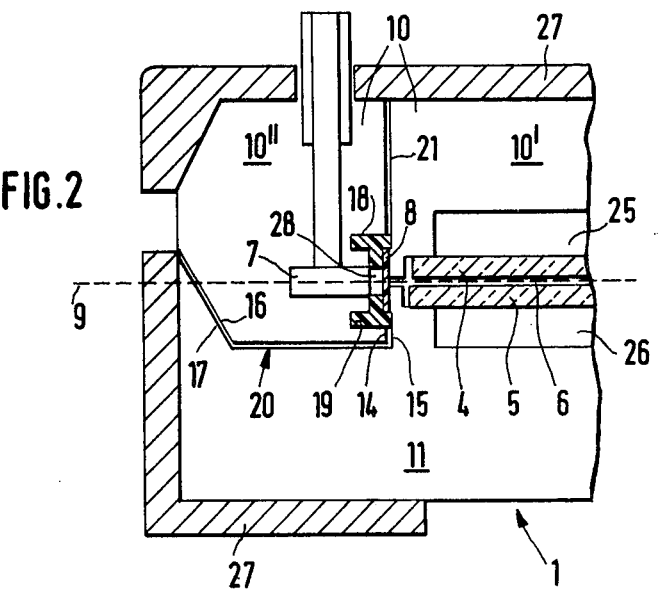

DEVICE FOR CONTINUOUS ELECTROPHORESIS IN A CARRIER FREE BUFFER CURRENT

The present invention is concerned with a device for continuous electrophoresis in a carrier free buffer current. The device includes a separation chamber, in which a separating space is located between two plane parallel glass plates held in a two-part frame. The separating space is separated from electrode chambers by permeable membranes.

Devices with a vertically installed separation chamber are known, where to achieve carrier free electrophoresis, an appropriate buffer is introduced into the separating chamber from above, and is sucked off at the underside. An electrical voltage is applied at both long sides of the separating chamber, whereby permeable membranes function to separate the separating space from the electrode chambers. There is a necessity to keep all interior walls of the separating space accessible for cleaning purposes, at the same time to seal the adjoining compartments carefully from each other. This sealing must not only reliably prevent the mixing of the various liquids in the separating space and the electrode chambers, but also prevent the straying of the electrical current. In order to fulfill this requirement, the known devices consist of numerous individual parts, which have to be braced and sealed with respect to each other. Since in using the separating chamber, a regular cleaning of the interior chamber is necessary, the known devices are not only expensive to build, but also awkward to use, since they require a time-consuming and work-intensive assembly and disassembly.

One of the known devices seeks to overcome these difficulties by giving the separating space, between the electrodes, not a plane but a simple or multiple-angular cross-section or an arched cross-section. The intention is to remove the critical electrode chambers and membrane sealings out from the chamber plane, and thus be able to leave them unchanged in the routinely required opening of the separating chamber. This construction, however, has the disadvantage that the electrical length of the separating chamber is substantially larger than the distance useful for the separation. Thus, to achieve the identical field intensity and separating distance, larger electrical voltages are necessary and a substantially larger electrical wattage is set free in the separating chamber. Since a rise in temperature has to be avoided, there are more problems with cooling.

The task of the present invention is thus to create a device of the kind described initially, which also permits easy assembly and disassembly of the separating chamber and a utilization of the entire lengthwise edges of the separating space, while perfectly sealing the separating space and the electrode chambers, and dividing it with the help of membranes.

According to the present invention, this task is solved by a dividing joint between the two parts of the frame which is situated at least in part at such an angle to the dividing plane of the frame, that when the parts of the frame are pressed together along the dividing joint with a force component in the direction of the dividing plane, the membranes, then, are pressed against surfaces of the frame-parts that are lying opposite each other, thus forming a seal. On account of the at least partially angular course of the dividing joint, pressure of one surface of one frame-part against the membrane creates by necessity a perfect seal when the frame-parts are put together. Putting together and taking apart the frame-parts has been structured for ease; they only have to be juxtaposed and braced against each other. The bracing is perpendicular to the dividing plane.

The membranes may be arranged at least in part in the segment of the dividing joint running at an angle to the dividing plane, between facing, inclined planes of the frame parts, thus forming a seal. One of the frame-parts projects with a segment essentially trapezoidal in its cross-section into a cut-out of the other frame-part, in whose inclined plane the membranes are arranged. The membranes thus are at an angle to the dividing plane of the frame and define in this angular position the side of the separating space of the separating chamber.

An alternate solution may consist of the membranes being arranged, at least partially, in a segment of the dividing joint perpendicular to the dividing plane, between facing, normal planes of the frame-parts, thus forming a seal. One frame-part is divided into two segments by a further dividing joint in an extension of the segment of the dividing joint running perpendicular to the dividing plane, these two segments being kept movable against each other. The outer frame-segment has an inclined plane facing the membrane, which (inclined plane) interacts with an angular part of the dividing joint of the other frame-part. This arrangement is based on the same principle of solving the problem (exerting a force-component in the direction of the dividing plane which furthers the sealing, by putting together the frame-parts in a motion perpendicular to the dividing plane). In addition, it has the further advantage, that the membrane runs perpendicular to the dividing plane, i.e., that the separating space is defined along it lengthwise edges, not at an angle, but straight. In this context, the terms inclined planes and normal planes imply that the corresponding planes formed at the frame-parts run either at an angle or normal (perpendicular) to the dividing plane of the frame of the separating chamber. The inclined planes of the frame-parts facing each other may have slightly different angles, so that the desired contact pressure will result.

The membranes preferably should be arranged, as is known, in one surface of a packing strip of springy material. In a special form of construction of the present invention, the packing strips and/or the membranes project slightly over their respective plane of installation. In this way, it is possible to give an identical angle to the inclined planes of the frame facing each other, which assure the sealing function. Thus, when interlocking the frame-parts, the parts of the planes facing the membranes or packing strips respectively, will necessarily touch the front surface of the membranes or packing-strips respectively, and because of the use of springy material for the packing strips, the latter will be pressed together slightly up to the extent that they project over the plane of installation.

in one form of construction of the present invention, the packing strips are arranged each in a groove, which partially opens into the inclined plane of one of the frame-parts facing the separating space, and one segment of which partially projects sideways at an angle into the frame-part. The surface of the membrane or of the packing strip, respectively, thus is exposed in the area necessary for its intended contact with the facing surface area of the other frame-part. The remaining portion of the membrane or packing strip, respectively, is embedded in a segment of the groove, so that a secure position in the groove is assured when the chamber is opened.

The installation of the groove for the packing strips and the removal of the packing strips out of the groove for cleaning purposes or for a replacement, is improved in the previously discussed version by means of a further dividing joint, which divides one frame-part into two segments which partially extends (as an extension of the segment of the groove) sideways and at an angle into the one frame-part. The two segments may be firmly fastened to each other, e.g. screwed together, when the device is in operation. But the two segments could also be kept movable in regard to one another, the outer segment could have an inclined plane facing away from the membrane, which would interact with an inclined plane, facing the membrane, of the other frame-part. These inclined planes facing each other bring about an improvement of the sealing function as well, especially when they have a different inclination.

The version in which the membranes are arranged at least in part in a segment of the dividing joint perpendicular to the dividing plane (between facing normal planes of the frame-parts, thus forming a seal), could provide for each of the packing strips to be arranged in a groove (which opens partially into the normal plane facing the separating space) of one of the frame-parts, and partially into the further dividing joint. This will assure that the packing-strips with the membranes will keep their firm fit in the groove, when the separating chamber is being opened.

The glass plates are each held in a staggered recess of the frame-parts between the membranes; each area of recess behind the glass-plates serves as a flow chamber for coolant.

The frame-parts preferably should be held in metal corner braces. These serve to strengthen the frame-parts, which are made out of a transparent plastic material, when braced against each other. The corner braces are firmly attached to the frame-parts, but they could also form inclined planes with the frame-parts according to the invention, so that in this latter case the angular part of the dividing joint can be eliminated, however the necessary cross or horizontal dividing joints must be provided in this form of construction.

Additional characteristics, advantages, and possible applications of the present invention will become apparent from the following description of the preferred forms of construction with the help of the accompanying drawing, in which:

FIG. 1 shows the right half of a horizontal cross section through a separating chamber according to the present invention; and FIG. 2 shows the left half of a horizontal cross section of a separating chamber according to an alternate version of the present invention.

A separating chamber 1, according to FIG. 1, has two frame-parts 10 and 11, capable of being taken apart, and preferably made out of transparent plastic material. Two plane parallel glass plates 4 and 5 are held by conventional means in staggered recesses 25 and 26 of the frame-parts 10 and 11, and define between them the separating space 6. The edges of glass plates 4 and 5 are preferably glued into the frame parts 10 and 11. The front or inner faces of the glass plates 4 and 5 align with the neighboring surfaces of the frame-parts 10 and 11, so that the separating space 6, defined by the glass plates 4 and 5, extends evenly in the direction of the electrode chambers 7. The electrode chambers 7 extend along the side edges of separating space 6 and is separated therefrom by a permeable membrane. The parts of the recesses 25 and 26 situated behind the outer faces of the glass plates 4 and 5 serve as flow chambers for coolant.

Between the two frame parts 10 and 11 there is, in continuation of the actual separating space 6, a dividing joint 20. The dividing joint 20 extends in one part at an angle to the dividing plane 9, i.e. in this area the frame-parts 10 and 11 includes inclined planes 12 and 13 facing each other. The dividing plane 9 passes between the inner faces of the glass plates and is parallel thereto. A groove 19, provided in the inclined plane 12, extends sideways in a segment 19' into the frame-part 10 at an angle.

A packing strip 18 made of conventional springy material is installed in groove 19, and carries and maintains in its surface area the permeable membrane 8. The packing strip 18 has a slotted aperture 28, which is covered by membrane 8, so that the separating space 6 and the electrode chamber 7, abutting the slotted aperture 28, are separated only by membrane 8. The packing strip 18 with the membrane 8 projects slightly over the surface plane 12. When joining frame-parts 10 and 11, the inclined plane 13 lies against the surfaces of packing strip 18 and membrane 8 to provide a secure seal. To enhance the sealing function, the inclined planes 12 and 13 may have a different inclination.

On the other side of the slotted aperture 28, the packing strip 18 with the membrane 8 is embedded in the segment 19' of the groove 19, so that in this way the sealing function is satisfactorily assured. A further dividing joint 22 may abut the groove section 19', so that segment 10" of the frame-part 10, which contains the groove 19 with the packing strip 18 and the membrane 8, may be removed from the other segment 10'. In this way, the groove segment 19' may be more easily produced, and the packing strip 18 with the membrane 8 more easily replaced. Should the packing strip 18 with membrane 8 not be made replaceable, then the two segments 10' and 10" of frame-part 10 may be attached to each other firmly, e.g., screwed together.

If there is a dividing joint 22, then the outer edge of the dividing joint 20 can form the facing, inclined planes 23 and 24 of the frame-parts 10 and 11, which, just as the inclined planes 12 and 13, improve the sealing function when the frame-parts 10 and 11 are joined, since a force component situated in the direction of dividing plane 9 is created between the packing strip 18 and membrane 8 on the one hand, and the opposite contact surface 13 on the other. Frame-parts 10 and 11 are held in metal corner braces 27, for the purpose of strengthening them. The inclined planes provided between the corner brace 27 and the frame-part 10, can carry out the function, according to the present invention, of the angular part of the dividing joint 20 either in full or in part, as long as the corner brace 27 is not firmly joined to frame-part 10 and there is a dividing joint 22.

FIG. 2 represents as alternate form of construction of the present invention. This version, though similar to the one disclosed in FIG. 1, basically differs therefrom by the fact that the membrane 8 defines the sides of the separating space 6 in a plane perpendicular to the dividing plane 9. The two frame-parts 10 and 11 have for this purpose two facing normal plane surfaces 14 and 15 at the dividing joint 20. In extension of this dividing joint, the one frame-part 10 is divided into two segments 10' and 10". Groove 19 is located in the outer segment 10" of frame-part 10 in such a way that it partially opens into the normal plane surface 14, which faces the normal plane surface 15 of frame-part 11, and partially opens into the further dividing joint 21. Thus, when joining segments 10′ and 10″, the packing strip 18 with the membrane 8, installed in the groove, is held securely even when the frame-part 11 is removed in order to clean the arrangement.

In order to maintain the contact pressure required at the sealing point of the normal plane surfaces 14 and 15, as well as of the dividing joint 21 with the membrane 8 in the direction of the dividing plane 9, the part of dividing joint 20 lying outside of the membrane arrangement is at an angle. This angle is formed by providing an inclined surface 16 facing away from the membrane, in the segment 10″ of the frame-part 10, and providing an inclined surface 17 facing membrane 8, in the frame-part 11. These inclined surfaces 16 and 17 may have slightly different inclinations, in order to produce the required contact pressure when frame-parts 10 and 11 are joined together.

A secure seal can also be obtained, either by itself or in addition, by having the packing strip 18 with membrane 8 project slightly over the installation plane and by making the packing strip out of the springy material, mentioned above. Just as in the arrangement of FIG. 1, the inclined planes provided between the corner brace 27 and the frame-part 10, can serve to create or improve the sealing function.

The packing strip 18 with the membrane 8 can be replaced easily by removing frame-part 11 and then taking apart sections 10′ and 10″ of the frame-part 10. Abutting the slot or aperature 28 of the packing strip 18 is the electrode chamber 7, just as in the version shown in FIG. 1. Here, however, the aperature 28 does not consist of an inclined slot, but in a slot lying in the dividing plane 9, i.e. in a straight prolongation of the separating space 6. The electrodes (not drawn in) could be metal strips glued to one of the side or back walls of the electrode chamber 7, just as in the version of FIG. 1.

This device for the continuous electrophoresis in the carrier free buffer current according to the present invention, is simple to produce and to operate while reliably fulfilling the necessary sealing function. The separating space 6 enclosed between membranes 8 extends evenly along the entire width of separation, so that it can be optimally utilized. In the lateral areas of separate space 6, no disadvantageous field inhomogeneities occur. The inside of separating space 6 is easily accessible for cleaning purposes and the optimal sealing effect is gained optimally by necessity after re-joining the frame-parts 10 and 11. The packing strip 18 with the membranes 8, too, can be easily exchanged, while at the same time being firmly secured when installed.

What is claimed is:

1. Device for continuous electrophoresis in a carrier free buffer current, said device comprising a separating chamber including a two-part frame, two plane parallel glass plates positioned in said frame, said glass plates defining a separating space therebetween, electrode chambers disposed in said frame and coacting with said separating space, permeable membranes separating said electrode chambers from said separating space, said frame having a dividing plane parallel to said glass plates, first surfaces of one frame part facing second surfaces of the other frame part to define a dividing joint between the two frame parts, said dividing joint being at least partially disposed at an angle to said dividing plane, and means for maintaining said membranes in said dividing joint to press said membranes against at least one of said first and second surfaces when said two frame parts are joined together for providing a seal which is effected by said angle.

2. A device according to claim 1, wherein at least part of said membranes are disposed in a segment of said dividing joint which is disposed at said angle.

3. A device according to claim 2, wherein said angle is a right angle with said parts of said membranes being disposed perpendicular to said dividing plane.

4. A device according to claim 3, wherein said one frame part is divided into two segments by a second dividing joint extending from a portion of said first-mentioned joint disposed at said right angle, said two segments being moveable against each other, an outer one of said two segments having an inclined surface facing away from said membranes, said inclined surface interacting with an inclined surface of said other frame part which faces said membranes along said first-mentioned joint.

5. A device according to claim 1, wherein each of said membranes is disposed on a surface of packing strip fabricated from springy material.

6. A device according to claim 5, wherein each of said membranes and packing strips project slightly over their respective installation planes.

7. A device according to claim 1, wherein each of said membranes is disposed in a groove which partially opens into an inclined surface of said one frame part facing said separating space, a segment of said groove projects partially sideways at an angle into said one frame part.

8. A device according to claim 7, wherein said groove segment extends to provide a second dividing joint separating said one frame part into two segments.

9. A device according to claim 8, wherein said two segments of said one frame part are firmly connected to each other when said device is in operation.

10. A device according to claim 8, wherein said two segments of said one frame part are moveable against one another, one of said two segments having an inclined surface facing away from said membranes and interacting with an inclined surface of said other frame part which faces said membranes.

11. A device according to claim 1, wherein each of said membranes is disposed in a groove which partially opens into a surface of said one frame part facing and normal to said separating space, said groove projecting partially into another dividing joint.

12. A device according to claim 1, wherein each of said glass plates is held in a staggered recess of said frame, between said membranes, remaining space in each recess behind associated glass plate serving as a flow chamber for coolant.

13. A device according to claim 1, wherein said frame is held in metal corner braces.

* * * * *